United States Patent
Budach et al.

(10) Patent No.: US 8,674,329 B2
(45) Date of Patent: Mar. 18, 2014

(54) METHOD AND APPARATUS FOR ANALYZING AND/OR REPAIRING OF AN EUV MASK DEFECT

(75) Inventors: Michael Budach, Hanau (DE); Tristan Bret, Darmstadt (DE); Klaus Edinger, Lorsch (DE); Thorsten Hofmann, Rodgau (DE); Heiko Feldmann, Aalen (DE); Johannes Ruoff, Aalen (DE)

(73) Assignees: Carl Zeiss SMS GmbH, Jena (DE); Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 13/805,960

(22) PCT Filed: Jun. 24, 2011

(86) PCT No.: PCT/EP2011/060626
§ 371 (c)(1),
(2), (4) Date: Feb. 28, 2013

(87) PCT Pub. No.: WO2011/161243
PCT Pub. Date: Dec. 29, 2011

(65) Prior Publication Data
US 2013/0156939 A1      Jun. 20, 2013

(30) Foreign Application Priority Data
Jun. 23, 2010   (DE) .......................... 10 2010 025 033

(51) Int. Cl.
*G21K 5/04*         (2006.01)
(52) U.S. Cl.
USPC .................... 250/504 R; 250/492.1; 359/350; 359/361

(58) Field of Classification Search
USPC ................... 250/492.1, 492.2, 493.1, 504 R; 359/350, 361; 430/5, 311, 394
See application file for complete search history.

(56) References Cited

U.S. PATENT DOCUMENTS

| | | | |
|---|---|---|---|
| 5,808,312 A | 9/1998 | Fukuda | |
| 6,016,357 A | 1/2000 | Neary et al. | |
| 6,235,434 B1 | 5/2001 | Sweeney et al. | |
| 6,844,272 B2 | 1/2005 | Taylor et al. | |

(Continued)

FOREIGN PATENT DOCUMENTS

| JP | 2008085223 A | 4/2008 |
|---|---|---|
| WO | WO 02/27404 | 4/2002 |

OTHER PUBLICATIONS

International Search Report and Written Opinion corresponding to PCT/EP2011/060626 dated Dec. 1, 2011.

(Continued)

*Primary Examiner* — Nicole Ippolito
(74) *Attorney, Agent, or Firm* — Fish & Richardson P.C.

(57) ABSTRACT

The invention relates to a method for analyzing a defect of a photolithographic mask for an extreme ultraviolet (EUV) wavelength range (EUV mask) comprising the steps of: (a) generating at least one focus stack relating to the defect using an EUV mask inspection tool, (b) determining a surface configuration of the EUV mask at a position of the defect, (c) providing model structures having the determined surface configuration which have different phase errors and generating the respective focus stacks, and (d) determining a three dimensional error structure of the EUV mask defect by comparing the at least one generated focus stack of the defect and the generated focus stacks of the model structures.

10 Claims, 8 Drawing Sheets

(56) References Cited

U.S. PATENT DOCUMENTS

| | | | |
|---|---|---|---|
| 6,849,859 B2 | 2/2005 | Folta et al. | |
| 2004/0051857 A1* | 3/2004 | Hudyma et al. | 355/67 |
| 2005/0157384 A1 | 7/2005 | Shiraishi et al. | |
| 2005/0173384 A1 | 8/2005 | Coelho et al. | |
| 2005/0185173 A1 | 8/2005 | Hau-Riege et al. | |
| 2006/0007433 A1* | 1/2006 | Ikuta et al. | 356/237.2 |
| 2008/0318138 A1* | 12/2008 | Holfeld | 430/5 |
| 2009/0286166 A1 | 11/2009 | Sugiyama et al. | |
| 2009/0297988 A1 | 12/2009 | Tanaka | |

OTHER PUBLICATIONS

Sungmin et al., "Study of Real Defects on EUV Blanks and a Strategy for EUV Mask Inspection," May 2010, pp. 1-8, XP002659236, ISSN: 0277-786X.

Clifford et al., "Comparison of fast 3D simulation and actinic inspection for EUV masks with buried defects," May 2009, XP002659235, pp. 1-10.

Terasawa et al., "Actinic phase defect detection and printability analysis for patterned EUVL mask," Mar. 2010, pp. 1-10, XP002659237, ISSN: 0277-786X.

Clifford et al., "Compensation methods for buried defects in extreme ultraviolet lithography masks," Mar. 2010, pp. 1-8, XP002659238, ISSN: 0277-786X.

"Study of critical dimensions of printable phase defects using an extreme ultraviolet microscope" by Kinoshita et al., Jpn. J. of Appl. Phys. 48 (2009), pp. o6FA07-1-06FA07-4.

Thesis of C.H. Clifford: "Simulation and compensation methods for 25 EUV lithography masks with buried defects", Electrical Engineering and Computer Sciences, University of California at Berkeley, May 12, 2010, Techn. Report No. UCB/EECS-2010-62.

"Natural EUV mask blank defects: evidence, timely detection, analysis and outlook" by D. van den Heuvel et al., SPIE/BACUS Conf. Proc. 2010.

SRIM "The Stopping and Range of Ions in Matter", 1page, downloaded from "http://www.srim.org/SRIM/SRIMINTRO.htm" on Dec. 20, 2012.

Excerpts of SRIM "The Stopping and Range of Ions in Matter" by J.F. Ziegler, J.P. Biersack, and U. Littmark, Pergamon Press, New York, 1985, pp. 1-15, downloaded from "http://www.srim.org/SRIM%20Book%20%28Review%20Pages%29.htm".

* cited by examiner

METHOD AND APPARATUS FOR ANALYZING AND/OR REPAIRING OF AN EUV MASK DEFECT

CROSS-REFERENCE TO RELATED APPLICATIONS

This application is a national stage application of PCT/EP2011/060626, filed on Jun. 24, 2011, which claims priority to German Application 10 2010 025 033.3, filed on Jun. 23, 2010, herein incorporated by reference in its entirety.

1. FIELD OF THE INVENTION

The present invention relates to the field of analyzing and/or repairing of an EUV mask defect.

2. BACKGROUND OF THE INVENTION

As a result of the shrinking sizes of integrated circuits, photolithographic masks have to project smaller and smaller structures onto a photosensitive layer i.e. a photoresist dispensed on a wafer. In order to enable the decrease of the critical dimension (CD) of the structure elements forming the integrated circuits (ICs), the exposure wavelength of photolithographic masks has been shifted from the near ultraviolet across the mean ultraviolet into the far ultraviolet region of the electromagnetic spectrum. Presently, a wavelength of 193 nm is typically used for the exposure of the photoresist on wafers. As a consequence, the manufacturing of photolithographic masks with increasing resolution is becoming more and more complex.

In the future, photolithographic masks will use even smaller wavelengths in the extreme ultraviolet (EUV) wavelength range of the electromagnetic spectrum. The term EUV mask denotes in the following a photolithographic mask for the EUV wavelength range (preferably 10 nm to 15 nm).

The optical elements for the EUV wavelength range will preferably be reflective optical elements. For the fabrication of an EUV optical element a multilayer structure or a multilayer film is deposited on a substrate having an ultralow thermal expansion (ULE). Fused silica is an example of a substrate used for EUV optical elements. The multilayer system typically comprises 80 to 120 alternating layers of molybdenum (Mo) and silicon (Si). A pair of a Mo—Si layer or a Mo—Si bilayer has a depth of approximately 7 nm. At the boundary of the Mo—Si layers a portion of the incident EUV radiation is reflected, so that a Mo—Si multilayer layer system ideally reflects more than 70% of the incident EUV radiation.

In addition to the multilayer structure, an EUV mask comprises a pattern or an absorbing pattern structure on top of the multilayer. For example, the EUV radiation absorbing pattern can be formed of titanium nitride, tantalum nitride, or chromium. The interaction of the EUV radiation absorbing portions and EUV radiation reflecting portions of the EUV mask generates in case of an illumination with EUV radiation the pattern to be presented in the photoresist dispensed on a semiconductor wafer.

Highest precision is required at the fabrication of EUV optical elements, in particular for EUV masks. Errors in the order of 1 nm can already cause errors in the image of the pattern structure on the wafer. Mask errors or defects which are apparent on the pattern of the wafer generated by the mask are called printing errors. Defects of different types can occur at various positions of the EUV mask leading to various effects.

EUV inspection and review systems operating at the illumination wavelength are already known. The U.S. Pat. Nos. 6,954,266, or 5,808,312 describe EUV inspection and review systems or tools operating in combination with a mask repairing system. EUV review systems are also denoted as EUV mask inspection microscopes (EUVM).

Further investigation methods for EUV masks are also known. The US 2009/0 286 166 discloses the use of an atomic force microscope (AFM) for the localization of concave defects on EUV masks. The U.S. Pat. No. 6,844,272 describes the determination of the height of the surface of EUV masks by the use of an interferometer.

Defects of the absorbing pattern structure may occur if absorbing material is missing at positions which should be opaque, or when absorbing material is existent at positions which should be dear. Further, dirt particles may be attached to the surfaces of EUV optical elements. This type of error results predominantly in amplitude errors. It can be recognized by a surface analysis of the EUV optical element; for example by using a scanning electron microscope (SEM). Using a known mask repairing system, as for example the MeRiT® system of Carl Zeiss SMS excessive material can be removed. An electron beam in combination with a suitable etching gas can be used for this task. Missing absorber material can for example be added by locally depositing chromium with the aid of an electron beam together with a respective precursor gas.

EUV optical elements can be washed or polished in order to dean their surfaces from disturbing particles or substances.

On the other hand, so-called buried defects can occur in EUV optical elements, i.e. EUV mirrors and/or EUV masks. In the following, the term "buried defect" means a defect or an error which is located on the substrate and/or within the multilayer structure of the EUV optical element. Buried defects lead to both, amplitude and phase errors, i.e. buried defects comprise amplitude and phase error portions. Buried defects are also called topological errors.

The U.S. Pat. No. 6,016,357 describes a method for correcting errors of the absorbing pattern structure by the measurement of focus stacks in phase shift masks (PSM) illuminated with deep ultraviolet (DUV) radiation. Further, this document describes a repairing method for removing excessive absorbing materials and for depositing missing absorbing material. This repairing method is denoted as compensational repair.

The U.S. Pat. No. 6,235,434 describes the repair of amplitude and phase errors of EUV masks. Independent of the type of error, the repair is done by compensation, i.e. correcting of the absorbing pattern by removing excessive material from the absorbing pattern structure or depositing absorbing material to the absorbing pattern structure, respectively. Further, the US 2005/0 157 384 also discloses the removal of material, whereas the U.S. Pat. No. 6,849,859 describes the adjustment of a thickness of a layer by depositing an additionally layer and by adjusting the thickness of the additional layer.

When excessive absorbing material is removed by an ion beam, ions are implanted in a buffer layer arranged between the multilayer film and the absorbing pattern structure. The implanted ions may vary the reflectivity of the corrected EUV mask portion. The JP 2008 085 223 A discloses a method to correct the reflectivity change induced by the implanted ions by respectively correcting the absorbing pattern structure.

The article "Study of critical dimensions of printable phase defects using an extreme ultraviolet microscope" by Y. Kamaji et al., Jpn. J. of Appl. Phys. 48 (2009), pp. 06FA07-1-06FA07-4 explains why pits are more often defects in multilayer films of EUV masks than bumps. Further, the article reports on the fabrication of programmed phase defects and their analysis in order to determine the resolution limit of an EUV microscope (EUVM).

The thesis of C. H. Clifford: "Simulation and compensation methods for EUV lithography masks with buried defects", Electrical Engineering and Computer Sciences, University of California at Berkeley, Techn. Report No. UCB/EECS-2010-62 describes simulation methods which allow generating simulation configurations based on aerial images of defects. This document also reports on two methods for defect compensation by adjusting the absorber pattern of EUV masks.

The article "Natural EUV mask blank defects: evidence, timely detection, analysis and outlook" by D. van den Heuvel et al., SPIE/BACUS Conf. Proc. 2010, describes a method to combine aerial images, marks and AFM measurement data in order to localise and to measure an EUV defect which cannot be recognized in a scanning electron microscope (SEM). Moreover, this paper describes that both, pits as shallow as 3 nm and bumps just 3 nm high at the surface can results in critical printing defects buried in the multilayer.

Figure 1:
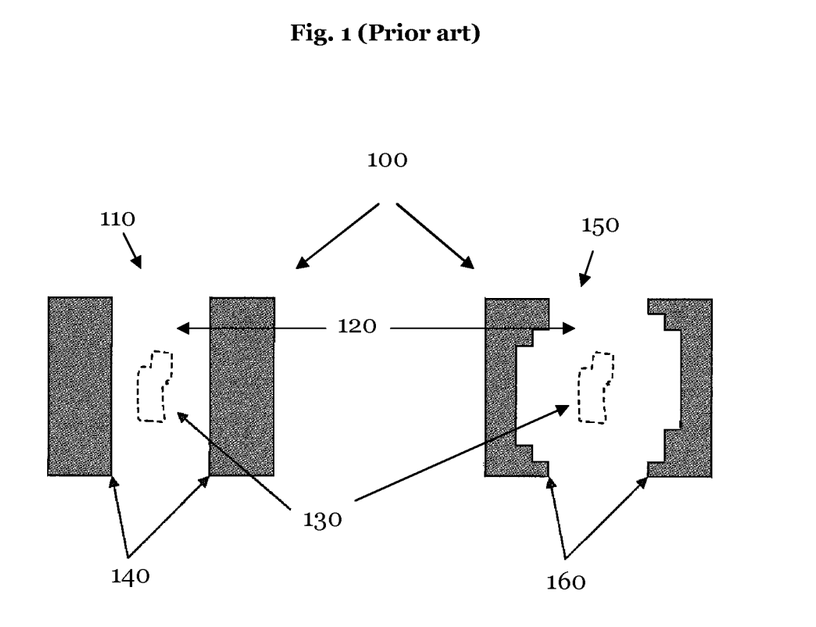
FIG. 1 schematically represents a compensational repair of a buried defect of an EUV mask according to the prior art.

The above mentioned documents do often not clearly distinguish between amplitude errors and phase errors of buried defects, i.e. of defects on substrates and/or multilayer films of EUV masks. The repair methods denoted as "compensational repair" addresses the amplitude error portions of buried defects, but ignores their phase error portions. FIG. 1 schematically illustrates the compensational repair of a multilayer defect by removing a portion of the absorbing pattern elements adjacent to the defect in order to compensate for the reduced reflectivity of the buried multilayer defect.

The compensational repair has the drawback that it results in a diminution of the process window at the wafer illumination, since an EUV mask compensated with this approach has a focus dependency which deviates significantly from the ideal focus characteristics. Moreover, the compensational repair method cannot be applied to correct defects in EUV mirrors not having an absorbing pattern structure.

It is therefore one object of the present invention to provide a method and an apparatus for analysing and/or repairing of a defect of an EUV mask, which at least partially overcome the above mentioned drawbacks of the prior art.

3. SUMMARY OF THE INVENTION

According to a first aspect of the invention, a method according to claim 1 is provided. In an embodiment, a method for analyzing a defect of a photolithographic mask for an extreme ultraviolet (EUV) wavelength range (EUV mask) comprises (a) generating at least one focus stack relating to the defect using an EUV mask inspection tool, (b) determining a surface configuration of the EUV mask at the position of the defect, (c) providing model structures having the determined surface configuration which have different phase errors and generating the respective focus stacks, and (d) determining a three dimensional error structure of the EUV mask defect by comparing the at least one generated focus stack of the defect and the generated focus stacks of the model structures.

The described method exploits that amplitude errors and phase errors become manifest in different focus characteristics. Therefore, the measured focus stack enables discriminating between amplitude errors and phase errors. Amplitude errors basically correspond to surface defects and phase errors basically corresponds to buried defects. Amplitude errors are corrected using a method known in the state of the art.

The surface configuration of an identified buried defect which demonstrates in a phase error is analyzed. From the measured surface configuration model structures are calculated from which a three dimensional (3D) error structure of the defect is determined.

Thus, the described methods define a procedure to reliably detect and discriminate defects of an EUV mask and to determine an individual 3D error structure of identified buried defects. The 3D error structure of the buried defect can be used to develop a repairing or a compensation policy individually designed for the analyzed buried defect.

An EUV mask is preferably a reflective optical element. However, it is also possible to apply the method defined in the first paragraph of this section to transmissive optical elements. Furthermore, the described method is not restricted for analyzing defects of EUV masks. In fact, it can also be applied to analyze defects of photolithographic masks or more general of optical elements designed for a longer wavelength range as well as for a shorter wavelength range.

In a further aspect determining the surface configuration comprises scanning the defect with an atomic force microscope, and/or with a scanning tunnelling microscope, and/or with a stylus profilometer, and/or with an interferometer.

After a phase error has been identified and localised by analysing a focus stack measured with a mask inspection tool, the surface of the EUV mask above the buried defect causing the phase error is scanned in detail in order to determine the surface configuration. The surface configuration corresponds to the surface topology at the defective position of the EUV optical element. The exemplary combination of both measurement data allows the determination of a 3D error structure for the analyzed defect.

Another aspect comprises the step of applying different repairing methods to the three dimensional error structure and simulating associated focus stacks in order to determine an optimal repairing method.

After having determined a 3D error structure, the effect of various repairing methods on the resulting focus stack can be evaluated by simulation prior to the application of the respective repairing method. A repairing method is identified by simulation which is optimally adapted to the analyzed defect prior to the correction of the defect. In particular, the described repairing method is not restricted to a modification of the pattern structure arranged on the multilayer film of an EUV mask. Rather, the defined repairing method explicitly includes a modification of the substrate and/or of the multilayer film of the EUV mask in order to correct analyzed defects not only of EUV mask but also of EUV mirrors.

Therefore, the defined method corrects buried defects instead of just compensating their amplitude error portion by a compensational repair.

In a further aspect determining the optimal repairing method comprises selecting one of the different repairing methods as the optimal repairing method which generates a focus stack which maximizes a process window for the EUV optical element at the illumination of a wafer.

The process window is maximized for the repairing method whose aerial images of the focus stack fulfill a predetermined critical dimension (CD) variation for the largest defocus range of the different repairing methods. The application of this optimization criterion maximizes the process window at the illumination of the corrected EUV optical element or which maximizes the depth of focus (DOF), which is of utmost interest for the application of the EUV optical element in a lithography system.

Another aspect comprises applying the optimal repairing method to the defective position.

The specific treatment of the defective position minimizes the influence of the defect on the image of the EUV pattern in the photoresist arranged on a wafer, so that the EUV optical element can again be utilized in the production process after the respective error handling.

In still a further aspect, the model structures comprise an absorbing pattern structure on a surface of the EUV mask.

The existence of an absorbing pattern structure facilitates the determination of model structures for a defective position, as the absorbing pattern structure can be used for the identification of the defect position on the surface of the EUV mask. Further, a modification of the pattern elements can also be part of the error correction process. On the other hand, it is not mandatory that the model structures of a buried defect comprise a pattern structure. Rather, the described method can also be applied to EUV mirrors which do not have an absorbing pattern.

Another aspect comprises providing the absorbing pattern structure from EUV mask design data and/or from of a recording of at least one image.

When the pattern data is available, it is used as input for the simulation process of the effects of the various repairing methods. On the other hand, if this information is not available, it can alternatively be obtained from the recording of an image of the pattern structure. A scanning electron microscope (SEM) can be used for recording an image of the pattern. It is also possible to use a combination of both methods in order to determine the pattern data of an EUV mask.

A further aspect comprises using a repairing method correcting the three dimensional error structure so that a resulting multilayer structure is at least approximately corrected to an ideal multilayer structure.

In contrast to a compensational repair which just modifies pattern elements when trying to compensate a buried defect, i.e. a multilayer and/or a substrate defect, the described method modifies the substrate and/or the multilayer in order to correct a buried error. Thus, the defined method allows correcting analyzed buried defects to a much higher amount than by a compensational repair, which just addresses the amplitude error portion of a buried defect. Consequently, the described method maximizes the process window of an EUV optical element at its use in a lithography system.

Another aspect comprises applying the repairing method directly onto the defective position of the EUV mask.

As already mentioned above, the described method analyzes the 3D error structure of a buried defect and corrects the defect by acting on the substrate and/or on the multilayer film instead of only partially compensating the defect by locally modifying pattern elements close to the buried defect.

According to another aspect, the repairing method comprises at least partially removing the multilayer structure, in particular drilling at least one hole into the multilayer structure.

By removing the portion of the multilayer structure which comprises the buried defect, the defect is also removed. Then a defect-free multilayer film can be newly deposited. Although, this procedure requires some efforts, it does not compensate the defect; rather it is removed by the repairing process.

In still another aspect, the repairing method comprises locally compacting and/or expanding the multilayer structure and/or of a substrate of the EUV mask or generally of an EUV optical element by locally focusing femtosecond laser pulses into the EUV mask.

The defined repairing method is an example of a repairing which directly corrects a buried defect by acting upon the substrate and/or the multi-layer film of the EUV optical element. In this context, a variation of the substrate is preferred, because the impact of the repair of the defect on the multilayer can be minimized.

In another aspect, the femtosecond laser pulses are incident through the substrate of the EUV mask.

When the femtosecond laser pulses are directed through the substrate to the defective position, the multilayer or at least the most important upper Mo—Si layers of the multilayer film are not or at least not significantly influenced by the correction of the buried defect.

According to a further aspect, an inspection microscope for photolithographic masks in the extreme ultraviolet wavelength range performs a method of any of the aspects described above.

According to a further aspect of the invention, a method according to patent claim 11 is provided. In an embodiment, a method for repairing a buried defect in an extreme ultraviolet (EUV) optical element comprises directing an ion beam onto the buried defect so that an ion dose is implanted in the EUV optical element suitable to locally change a volume of the EUV optical element.

The EUV optical element comprises an EUV mirror having a substrate and a multilayer structure and/or an EUV mask having a substrate, a multilayer structure and an absorbing pattern structure.

The inventive method corrects buried defects of EUV optical elements by directly modifying the substrate and/or the multilayer instead of just compensating the amplitude error portions of these defects by applying a compensational repair. Thus, the inventive method can not only be applied to EUV masks, but it can also be used to correct buried defects of EUV mirrors.

EUV optical elements will probably be reflective optical elements. However, the inventive method is not restricted to reflective optical elements, but can also be applied to transmissive optical elements. Moreover, the defined method is also not limited for the correction of buried errors of EUV optical elements. Rather, it can be applied to compensate buried defects of optical elements designed for longer as well as for shorter wavelengths.

In still a further aspect, the ion beam comprises inert gas ions, preferably noble gas ions, and most preferably helium ions.

Inert gas ions have the advantage that they do not react with the material into which they are implanted. This means, the mechanical and/or the optical properties of the substrate and/or the multilayer film are not significantly modified as a consequence of implanting ions. Further, the noble gas characteristics of the inert gas ions also prevents that the EUV photons of the lithography system induce a reaction of the implanted inert gas with the surrounding material during the operation of the EUV optical element which could change its optical properties in the course of time.

A further aspect comprises adapting an ion beam energy to a depth of the buried defect below a surface of the EUV optical element. In yet another aspect, the ion beam energy comprises a range of 1 keV to 200 keV, preferably 5 keV to 100 keV, and most preferably of 10 keV to 50 keV.

Ions are implanted in the EUV optical element with a specific spatial distribution. The spatial distribution as well as the maximum of the distribution depend on the energy with which the ions hit on the EUV optical element. The distribution of the implanted ions in beam direction is in the following called depth distribution. The energy with which the ions impinge of the EUV optical element can be selected so that the maximum of the depth distribution of the implanted ions fits to the depth of the buried defect.

In still another aspect, the EUV optical element comprises a multilayer structure and the energy of the ion beam is selected such that the ions are essentially implanted below layers of the multilayer structure of the EUV optical element which determine its reflective properties.

The term "essentially" means here as well as at further positions within this specification that the maximum and/or the width of the depth distribution are adjusted to the respective Mo—Si layers so that these layers comprise the majority of the implanted ions.

As already mentioned in the second section, ions implanted in the multi-layer structure may locally change the reflectivity of EUV photons and may such form an amplitude error. It is well known that a multilayer film shows an asymptotic reflectance characteristic. This means that the Mo—Si layers close to the surface of the EUV element account for the major portion of the reflected EUV radiation, whereas layers close to the substrate only insignificantly contribute to the reflectivity of the EUV optical element. Consequently, ions implanted in the lower Mo—Si layers (the Mo—Si layers dose to the substrate) can efficiently correct a buried defect without essentially influencing the reflective properties of the EUV optical element.

In a further aspect, the EUV optical element comprises at least one capture layer arranged between the substrate and the multilayer structure, and wherein ion beam energy is adjusted so that the ions are essentially implanted in the at least one capture layer.

By implanting the majority of the ions in the capture layer the reflective properties of the multilayer structure is not or at least not significantly changed. A defect located on the substrate surface in the Mo—Si layers close to the substrate may propagate through at multilayer and thus affecting its reflective characteristic. Therefore, by implanting the majority of the ions in a capture layer, a buried defect can efficiently be removed, so that the defect correction process does not significantly influence the reflective properties of the multilayer structure.

Still a further aspect comprises arranging a local protection layer on a surface of the EUV optical element through which the ion beam is directed when repairing the defect prior to directing the ion beam onto the defect and removing the local protection layer at the end of the repairing.

Ions impinging on an EUV optical element have a sputter effect on the surface of the EUV optical element, i.e. they have an energy to remove atoms from the surface of the EUV optical element. Hence, the impinging ions may damage the surface of the EUV optical element. This effect can be avoided by locally arranging of a protection layer on the multi-layer prior to the ion bombardment and by removing the protection layer at the end of the defect repairing process.

In accordance with a further aspect, the ion beam is not perpendicularly directed through a surface of the EUV optical element onto the buried defect.

As already mentioned, beside the sputter effect, ions may induce damages in the multilayer along their paths from the multilayer surface to their implanted position. By using an inclined incidence for the ion beam, a portion of the EUV optical element can be selected for the paths of the ions which has less impact on the imaging of the mask pattern on the wafer. In particular, an incidence angle can be chosen so that the ion beam incidents on an absorbing element. By this approach the multi-layer structure above a buried defect is not damaged during the repairing of the defect.

In yet another aspect, the buried defect is a concave defect, in particular a pit and/or a scratch and the local volume change comprises a local volume increase, in particular a local height increase. According to another aspect, the buried defect is a convex defect, in particular a bump and the local volume change comprises a local volume decrease, in particular a local height decrease.

Moreover, still a further aspect comprises the step of analyzing the buried defect with a method of any of the aspects described above.

Finally, according to another aspect, a focused ion beam apparatus performs a method of any of the aspects described above.

4. DESCRIPTION OF THE DRAWINGS

In order to better understand the present invention and to appreciate its practical applications, the following figures are provided and referenced hereafter. It should be noted that the figures are given as examples only and in no way limit the scope of the invention.

5. DETAILED DESCRIPTION OF PREFERRED EMBODIMENTS

In the following, the present invention will be more fully described with reference to the accompanying figures, in which exemplary embodiments of the invention are illustrated. However, the present invention may be embodied in different forms and should not be construed as limited to the examples set forth herein. Rather, these examples are provided so that the disclosure will be thorough and will convey the scope of the invention to persons skilled in the art.

FIG. 1 shows a top view of a cut-out of an EUV mask 100. The left diagram no comprises a multilayer structure 120 which has a multilayer defect 130 buried in the multilayer structure 120, which is called a buried defect. On the multilayer 120 two pattern elements 140 are arranged having a form of absorbing stripes. The right diagram 150 illustrates the absorber structure 160 of the left diagram no of the EUV mask 100 after the multilayer defect 130 of has been partially compensated by removing a portion of the absorbing material of the pattern elements 160 around the buried defect 130 in order to compensate the reduced reflectance of the area covered by the buried defect 130. As already mentioned in the third section, this approach of buried defect repairing is called "compensational repair".

Figure 2:
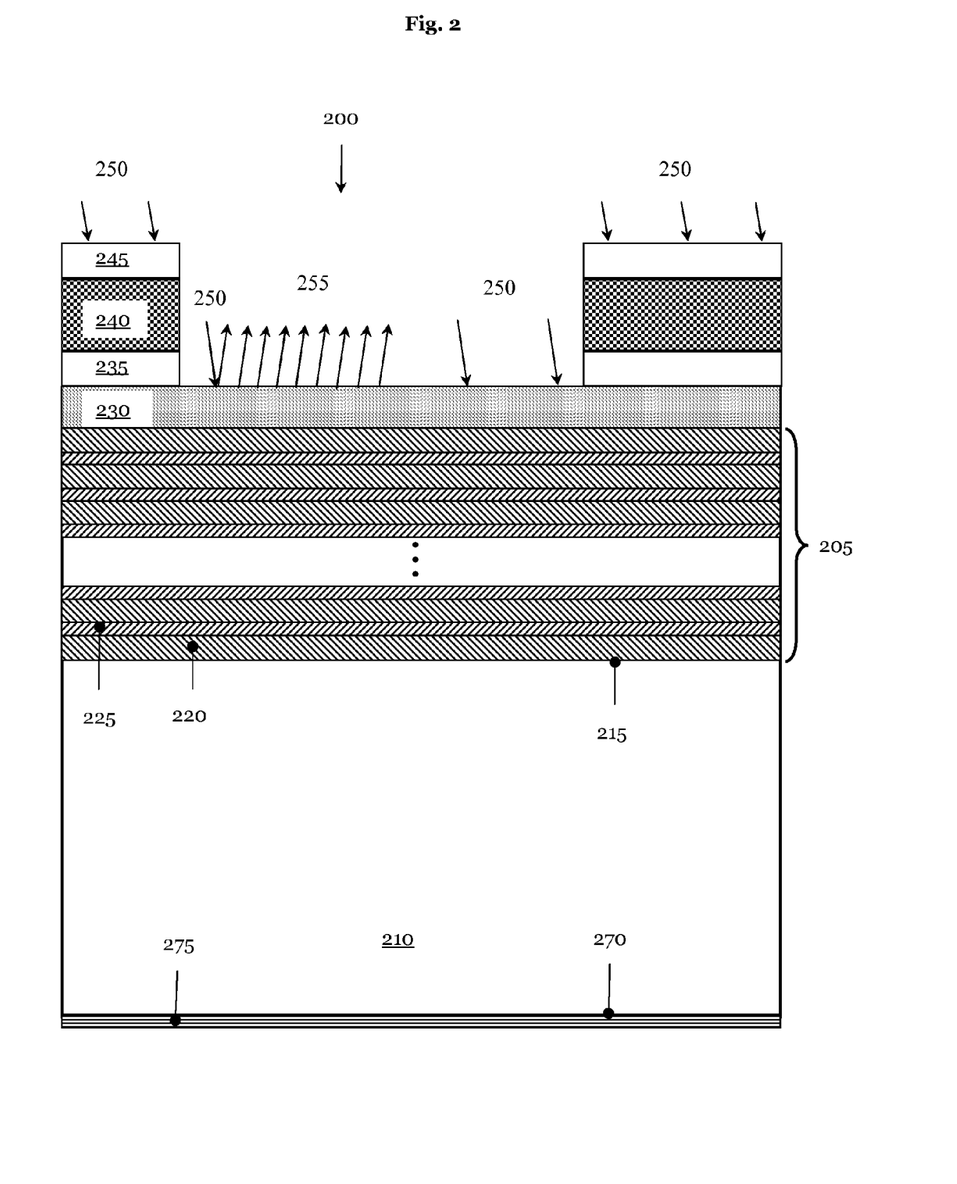
FIG. 2 schematically shows a sectional view of an EUV photolithographic mask.

FIG. 2 shows a schematic cross-sectional view of a photolithographic mask 200 for an exposure wavelength of 13.5 nm. Different from presently applied photolithographic masks, the EUV mask 200 is a reflective optical element based on a multilayer structure 205. The multilayer structure 205 acts as a mirror which selectively reflects incident EUV photons. The multilayer structure 205 of the EUV mask 200 is deposited on a front substrate surface 215 of a suitable substrate 210, such as a fused silica substrate. Other transparent dielectrics, glass materials or semiconducting materials may also be applied as substrates for photolithographic masks as for example ZERODUR®, ULE® or CLEARCERAM®. It is preferred that the material of the substrate 210 has a very low thermal expansion coefficient.

The multilayer film or multilayer structure 205 comprises 40 to 60 pairs of alternating molybdenum (Mo) 220 and silicon (Si) layers 225 (referred to in the following as Mo—Si layers). The thickness of each Mo layer 220 is 4.15 nm and that of the Si layer 225 amounts to 2.80 nm. In order to protect the multilayer structure 205, a capping layer 230 of silicon with a native oxide of 7 nm depth is arranged on top of the multilayer structure 205. Other materials can also be used for forming a capping layer 230 as for example ruthenium.

In the multilayer 205, the Mo layers 220 act as scattering layers, whereas the silicon layers 225 function as separation layers. For the scattering layers instead of Mo other elements with a high Z number may be utilized, such as cobalt (Co), nickel (Ni), tungsten (W), rhenium (Re) and iridium (Ir).

As already mentioned, the multilayer structure 205 on the substrate 210 of the EUV mask 200 acts as a mirror for EUV electromagnetic radiation. In order to become an EUV mask 200, a buffer structure 235 and an absorbing pattern structure 240 are additionally deposited on the capping layer 230. The buffer layer 235 may be deposited to protect the multilayer structure 205 during processing, for example during etching and/or repairing of the absorbing pattern structure 240. Possible buffer structure materials are for example of fused silica ($SiO_2$), silicon-oxygen-nitride (SiON), ruthenium (Ru), chromium (Cr), and/or chromium nitride (CrN). The absorbing structure 240 comprises a material having a large absorption constant for photons in the EUV wavelength range. Examples of these materials are chromium (Cr), titanium nitride (TiN) and/or tantalum nitride (TaN).

An anti-reflective (AR) layer 245 can additionally be arranged on the absorbing pattern structure 240 in order to secure that no photons are reflected by the surface of the absorber pattern 240. A material for an AR layer is for example tantalum oxynitride (TaON). A thickness of about 50 nm is sufficient to absorb basically all EUV photons 250 incident on the absorbing structure 240. In contrast, the majority of the photons 250 incident on the capping layer 230 is reflected as photons 255. In this context as well as on further positions of this description the term "basically" means a numeric value of a quantity within its measurement limit.

The substrate 210 of the EUV mask 200 has typical lateral dimensions of 152 mm×152 mm and a thickness or height of essentially 6.35 mm. The rear surface 270 of the substrate 210 or the rear substrate surface 270 has a thin metallic coating 275. Typically this coating 275 comprises chromium. The metallic coating 275 is used to fix the EUV mask 200 at the EUV scanner by the application of electrostatic forces.

Figure 3:
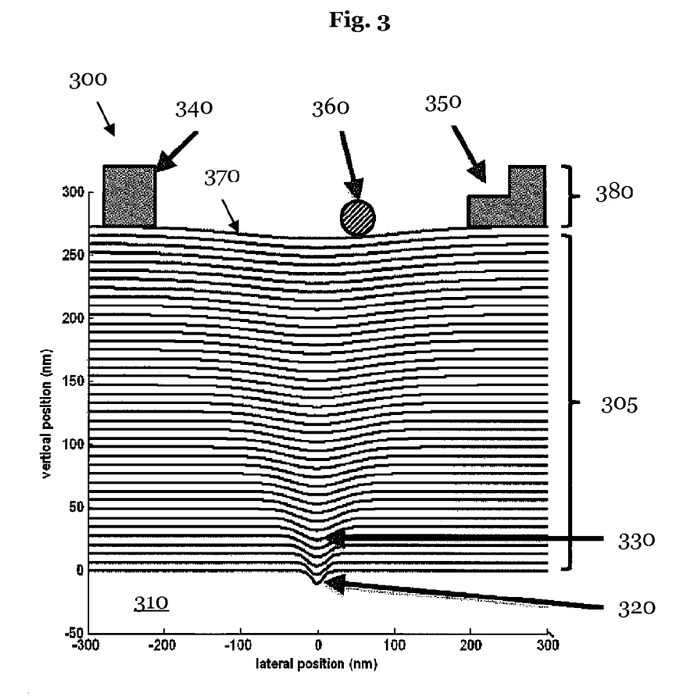
FIG. 3 schematically shows the EUV mask of FIG. 2 having various defects.

FIG. 3 represents the EUV mask 300 of FIG. 2 having various defects. In order to keep the following consideration simple, the capping layer 230, the buffer layer 235 as well as the AR layer 245 is omitted in FIG. 3. On the multilayer structure 305 an absorbing pattern 340 is deposited. The pattern element 350 of the absorbing pattern 340 has a portion which partially misses the absorbing material. Furthermore, a dirt particle 360 is attached on the surface 370 of the multilayer 305. The dirt particle 360 can be removed by a cleaning process, i.e. by washing and/or polishing the EUV mask 300. Both types of defect, absorber defects 350 and particle defects 360 on the surface 370 of the EUV mask 300 are in the following called surface defects 380.

The surface defects 380 can be detected by a surface analysis of the EUV mask 300. An electron beam of a scanning electron microscope (SEM) can for example be applied for the surface analysis of the EUV mask 300. Furthermore, the surface defects 380 are accessible to a repair by a modification of the absorbing pattern 340. As already mentioned in the second section, this can be performed by using a mask inspection and repairing system, as for example the MeRiT® system of Carl Zeiss SMS. Such a tool allows adding absorber material to the defective pattern element 350 by using an electron beam in combination with a suitable precursor gas or a combination of precursor gases. Examples of precursor gases are metal carbonyls, in particular dicobalt octacarbonyl ($Co_2(CO)_8$).

When the dirt particle 360 can not be removed by a cleaning process, the absorbing pattern 340 can be modified in order to compensate for the reduced reflectance in the area of multilayer 305 of the EUV mask 300 which comprises the dirt particle 360. This can be done by removing a portion the absorbing pattern 340 around the particle defect 360 as it is schematically indicated in FIG. 1 for the compensational repair of a buried defect 130. An electron beam together with an etching gas or a combination of etching gases can be applied in order to selectively remove a portion of the absorbing pattern 340. For example, xenon difluroride ($XeF_2$) can be used as an etching gas.

Further, the EUV mask 300 of FIG. 3 also shows a defect 320 in the substrate 310. In the example of FIG. 3, the substrate defect 320 is a pit or a scratch on the surface of the substrate 310. The substrate defect 320 propagates as defect 330 in the multilayer structure 305 of EUV mask 300. During its propagation through the multilayer structure 305, the multilayer defect 330 increases its lateral dimension, i.e. the distortion of the Mo—Si layers towards the multilayer surface extends on a larger area. At the same time, the variation of the height of the individual Mo—Si layers reduces during the propagation of the multilayer defect 330 through the multilayer structure 305. As indicated in FIG. 3, the substrate defect 320 of the substrate 310 is reflected in a shallow depression of the surface 370 of the multilayer 305 above the buried defect 320. The height variation of the depression at the surface 370 of the multilayer 305 may be as small as a few nanometers.

Figure 4:
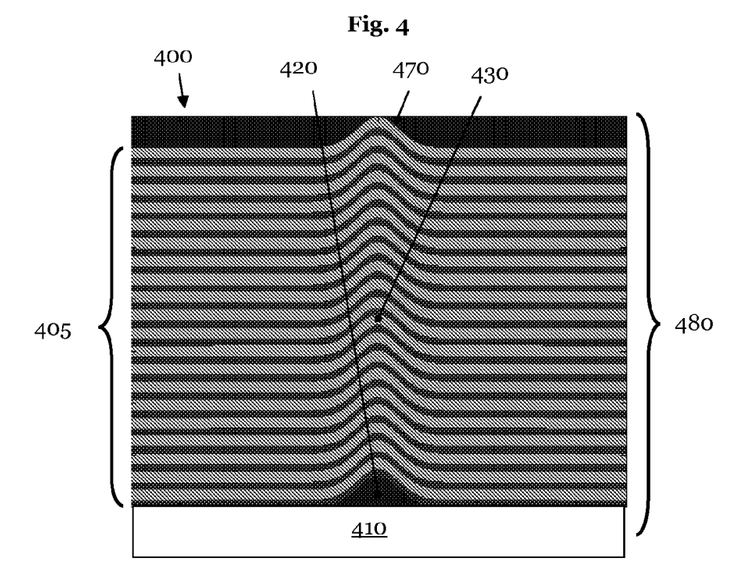
FIG. 4 schematically depicts a sectional view of the propagation of a buried defect on the substrate through various Mo—Si layers of the multilayer structure.

As discussed above, FIG. 3 represents a buried defect 320 caused by a pit or a scratch on the substrate 310. It is also possible that there is for example a dust particle on the surface of the substrate 310 at the beginning of the deposition of the multilayer 305. Furthermore, the substrate 310 may have a small local raise of its surface 370. FIG. 4 schematically depicts a cross section of a cut-out of an EUV mask 400 wherein a substrate 410 has a bump defect 420. Similar to the pit defect 320 of FIG. 3, the bump defect 420 propagates as multilayer defect 430 through the multilayer 405.

In addition to the substrate defects 320, 420, buried defects can also be localized in the multilayer 305, 405. For example, individual Mo and/or Si layers may have defective positions at which the width of one or several layers may deviate from its target value (not indicated in FIGS. 3 or 4). Moreover, it is conceivable that a dust particle on a specific Mo and/or Si layer may disturb the periodicity of successively deposited Mo—Si layers of the multilayer structure 305, 405. Similar to the substrate defects 320, 420, these local distortions of the periodicity of the multilayer structure 305, 405 can propagate towards the surface 370, 470 of the multilayer 305, 405.

In the following, defects of a substrate 310, 410 and defects within a multilayer structure 305, 405 are summarized as buried defects 480. In contrast to surface defects 380 which lead to amplitude errors on a wafer, buried defects 480 primarily result in phase errors at wafer illumination.

Although the substrate defects 320, 420 as well as the defects within the multilayer 305, 405 often become manifest only in a small local depression or a small local increase of the multilayer surface 370, these defects may cause printable errors on a wafer at its illumination.

The detection of the substrate defects 320, 420 or generally of buried defects 480 is involved. An electron beam of a SEM can neither detect the substrate defects 320, 420 nor the shallow depression or increase at the surface 370, 470 of the multilayer 305, 405 induced by the defects 320, 420. For example, an atomic force microscope (AFM) can detect the shallow variation of the surface 370, 470 of the multilayer system 305, 405. However, the substrate defects 320, 420 or generally the buried defect 480 causing a small local increase or depression have already been identified and localized by another metrology tool. Time constraints prevent to scan the overall EUV mask 300, 400 which an AFM.

Recording not only a single aerial image of the defective position of an EUV mask 300, 400 with a mask inspection tool, but recording of a set of aerial images through focus can reveal the buried defects 320, 420. For this purpose, an aerial image of the defective position is recorded in the best focus plane. Additionally, aerial images are recorded with a distance above and below to the focal plane, as for example ±15 nm, ±30 nm, ±45 nm, ±60 nm, and ±75 nm. In this example, the focus stack comprises 11 images. The number of images as well as the defocus distance can be adjusted to the analyzed defect.

Figure 5:
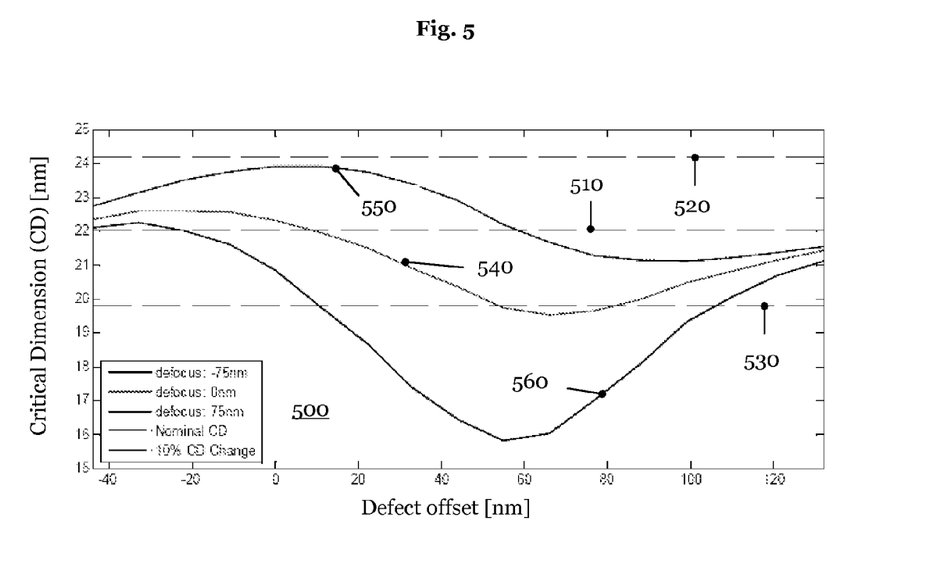
FIG. 5 schematically depicts a simulation of a critical dimension (CD) variation as a function of an offset (distance between the center position of the absorber element and the center of a pit defect) in focus and for defocus positions of ±75 nm.
Figure 6:
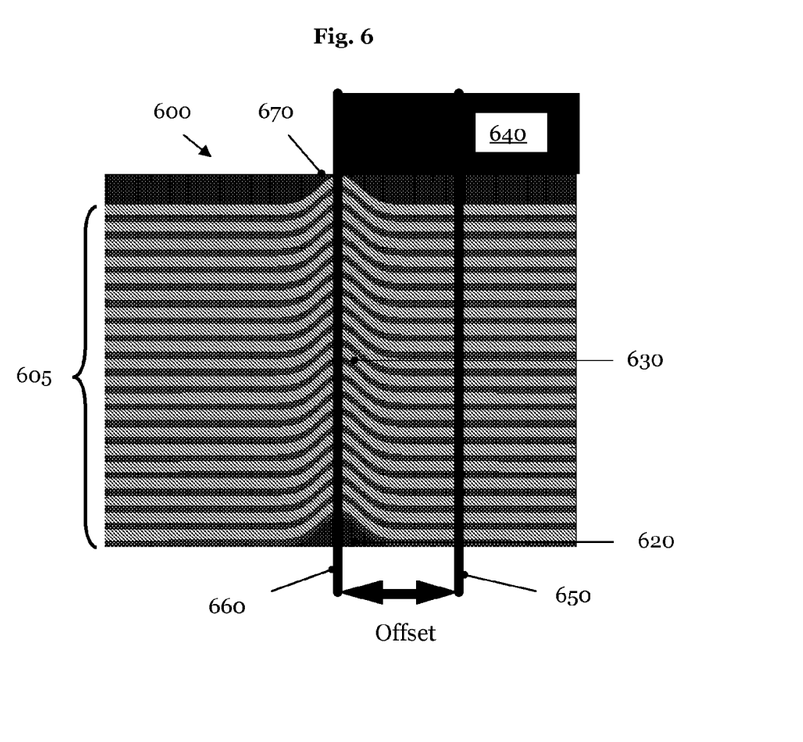
FIG. 6 schematically shows a sectional view of a cut-out of an EUV mask with a defect and an offset of the defect with respect to the center of a pattern element indicating the configuration simulated in FIG. 5.

FIG. 5 shows a diagram 500 of a simulation of the critical dimension (CD) variation as a function of the offset which is the distance between the center 650 of an absorbing pattern element 640 and the location 660 of the center of the defect 630. FIG. 6 illustrates the configuration simulated in FIG. 5. FIG. 6 depicts a multilayer structure 605 having a buried defect 620 similar to the bump defect 420 of FIG. 4. The bump defect 620 propagates as defect 630 towards the multilayer surface 680. The multilayer surface 670 has an absorbing pattern element 640. The center 650 of the absorbing pattern element 640 is the reference point 650 of the offset of or the distance to the center 660 of the defect 630. A shift of the buried defect 620 in the left direction in FIG. 6 results in FIG. 5 in a positive offset and vice versa.

In FIG. 5 the CD amounts to 22 nm as indicated by the vertical dashed line 510 at this CD numerical value. An upper dashed line 520 and the lower dashed line 530 represent boundary lines of a CD variation of ±10%. The curve 540 represents a simulation of the CD variation in focus as a function of the distance of the defect 620 from the center 650 of the pattern element 640. For an offset in the range between 60 nm and 80 nm the simulated CD variation is larger than 2.2 nm, i.e. the CD variation is larger than 10%. The curve 550 shows the simulated CD variation as a function of the offset for a defocus of +75 nm. For this defocus, the CD variation is within the ±10% CD variation bandwidth across the overall simulated offset. On the other hand, the curve 560 simulated with a defocus of −75 nm is for the larger portion of the simulated offset range beyond the tolerable CD variation of ±10%.

The simulated curves 540, 550, 560 indicate a strong dependence of the CD variation of the focus position. Such a behaviour is expected for a phase error as is indicated by the buried defect 620 in FIG. 6. FIG. 5 demonstrates that the measurement of aerial images of a focus stack or through focus can be used to discriminate between amplitude errors of surface defects 380 and phase errors of buried defects 480 of EUV masks 300, 400, 600.

The curves 540, 550 and 560 of FIG. 5 can be used for a compensational repair. An improvement of the in focus curve 540 can be obtained by modifying the pattern element 640 as schematically indicated in FIG. 1, so that the in focus curve 540 fulfils the ±10% variation criterion across the overall offset range. However, the CD variation of the defocus curves 550 and/or 560 may still be beyond the ±10% variation criterion. Thus, such a repairing diminishes the process window at the illumination of a wafer with the EUV mask 600. This situation is unsatisfactory; therefore a defect recognition method is necessary which analyzes a buried defect in detail. Further, a defect repairing method is required which repairs buried defects in such a way that the process window is as large as possible at the end of the repairing process.

The surface configuration of the EUV mask 300, 400, 600 is measured around the identified buried defect 320, 420, 620 for example with an atomic force microscope (AFM). Further tools which can be applied to scan the defective position are for example a scanning tunnelling microscope, a stylus profilometer, and/or an interferometer. The measured surface configuration allows the determination of the deviation of the measured surface configuration from an ideal surface configuration for the EUV masks 300, 400, 600.

In the next step, model structures are generated for various buried defects of an EUV mask. For the generation of the model structures, the data of the absorber pattern of the EUV mask at the defective position is required. This data is obtained from the design data of the mask, or it is obtained from the image recorded with an SEM.

Although the defect analysis is in the following explained for an EUV mask, it is appreciated that the described method can also be applied for the defect analysis of EUV mirrors. Moreover, the defined method is not restricted to the EUV wavelength range, but can also be utilized for the defect analysis of transmissive optical elements.

For each of the generated model structures aerial images for each focus position of a focus stack are simulated. In this simulation process, a plurality of the above discussed defects is considered for each surface configuration.

Then the measured surface configuration and the measured aerial images of the focus stack at the defective position are compared with the simulated aerial images of the focus stacks of the generated model structures. The model structure whose aerial images provide the best agreement with the measured aerial images across the focus stack is taken as the three dimensional (3D) error structure of the identified defect.

Finally, based on the determined 3D error structure, a repairing or compensation policy is developed which minimizes the impact of the 3D error structure of the EUV mask at the wafer illumination by a specific treatment of the defective position. The objective of the treatment is to again utilize the EUV mask in a production process for the wafer illumination at the end or the repairing process.

Two alternative approaches for the determination of a 3D error structure are conceivable: (a) if the measured aerial images of the focus stack indicate that the identified error is an amplitude error, the surface defect 380 causing the amplitude error can directly be corrected by varying the pattern structure 340, 640. This alternative does not analyze the surface configuration of the EUV mask around the detected surface defect 380 by scanning with an AFM.

(b) Irrespective of the identified error type, the surface configuration of the detected defect in scanned for example with an AFM in order to determine a surface configuration for a subsequent determination of a 3D error structure for each identified defect.

For the correction of the determined 3D error structure various repairing methods can be applied. As already mentioned above, a portion of an absorbing pattern structure can be removed by using an electron beam and/or an ion beam and as appropriate in combination with an etching gas or a combination of etching gases. Absorbing material can be removed in the vertical as well as in the horizontal direction.

Alternatively, absorber material, as for example chromium, may be added in both vertical and horizontal directions. The deposition can also be performed with an electron beam and/or with an ion beam and as appropriate together with a respective precursor gas or a combination of precursor gases. Both methods can be applied to correct surface defects 380 and may be employed for a compensational repair of buried defects 480 as schematically illustrated in FIG. 1.

A further repairing method comprises at least partially removing of the multilayer structure 305, 405, 605, as for example by drilling a hole into the multilayer structure 305, 405, 605 having a suitable dimension. If the portion of the multilayer structure 305, 405, 605 which comprises the buried defect 480 is removed, the defect 480 is also removed. Then a defect-free multilayer structure 305, 405, 605 can newly be deposited on the removed multilayer portion.

The effect of the repairing method described in the preceding paragraph is investigated by simulation prior to performing the replacement of a portion of the multilayer structure 305, 405, 605. This means, the intended correction is initially applied to the determined 3D error structure and a simulation of the resulting aerial images of the focus stack is performed. Only when the result confirms that the resulting aerial images of the corrected position have a sufficiently wide process window, the repairing method is really executed. If this is not the case, further simulations are performed with varied repairing methods or repairing parameters, respectively.

The parameters of a repairing method can be optimized by an iterative method. For example, if a buried defect 480 in a multilayer structure 305, 405, 605 is to be repaired by drilling of a hole into the multilayer 305, 405, 605, simulations are performed for holes having various depths, different diameters and/or having various distances from the buried defect.

For performing the above mentioned repairing methods an EUV mask inspection microscope is provided having an integrated repairing system. It is also possible to apply the defect analyzing and the defect repairing in separate systems.

A further repairing method comprises a local compaction and/or a local expansion of the substrate 310, 410 and/or of the multilayer structure 305, 405, 605 by the impact of electromagnetic radiation. The substrate 310, 410 and/or the multilayer structure 305, 405, 605 can for example be compacted or expanded by the usage of femtosencond laser pulses.

A compaction as well as an expansion of the various layers of an EUV optical element can also be achieved by implanting ions at a suitable position of an EUV optical element. In the example described in the following, the method is discussed in the context of a volume expansion. However, it is appreciated that the discussion of a volume expansion does not restrict the described method to volume expansion. Rather, it is also applicable to perform a respective volume compaction.

Figure 7:
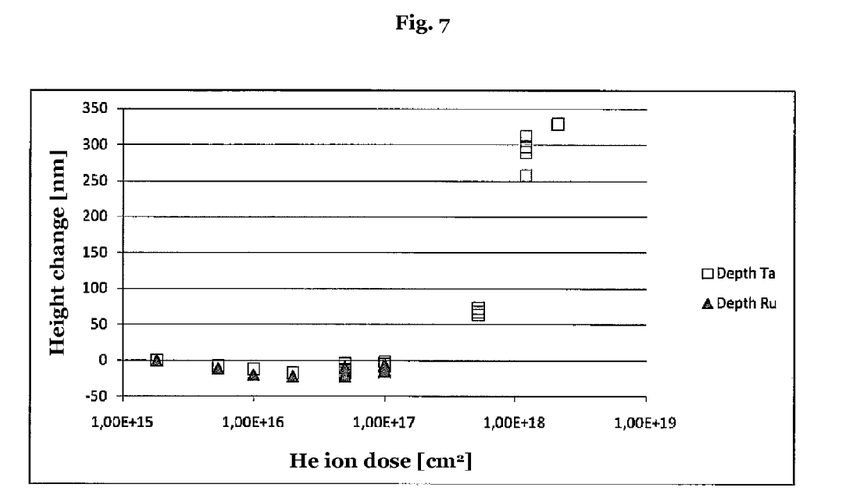
FIG. 7 schematically represents a height variation of an EUV mask surface as a function of an implanted helium ion dose.

FIG. 7 presents a curve which shows an induced change of the height of a photolithographic mask as a function of the implanted ion dose. In the example of FIG. 7, the mask was irradiated with a helium ion beam having a beam energy of 30 keV. As already mentioned, the helium beam or generally an ion beam has basically two effects: (a) a sputtering effect, i.e. (helium) ions collide with atoms of the sample and release atoms from the sample, (b) implantation, (helium) ions stay in the sample material.

In the example of FIG. 7, the implantation of helium atoms does basically not lead to a volume change below a built in ion dose of approximately $2 \cdot 10^{16}$ cm$^2$. Above this value the implantation of helium ions results in a volume expansion of the mask material which goes steeply up with an increase of the implanted helium dose.

FIG. 7 illustrates the interrelationship between a volume expansion of a photolithographic mask and the implanted ion dose for the example of helium ions. It is appreciated that similar curves also exist of other inert gas atoms, in particular for noble gas atoms.

The focussed ion beam of an ion beam (FIB) apparatus can be used in order to implant an ion dose in an EUV mask with a defined depth distribution as well as with a defined lateral distribution of the implanted ions. Alternatively, the FIB source can be integrated in the mask inspection tool which is applied for the defect analysis as discussed above. Furthermore, an AFM can for example be utilized to determine the volume change induced by the implanted ions. It is also possible to use one of the scanning tools or a combination of them mentioned in the context of the determination of the surface configuration in order to detect the local height change caused by the implantation of ions into an EUV mask.

Figure 8:
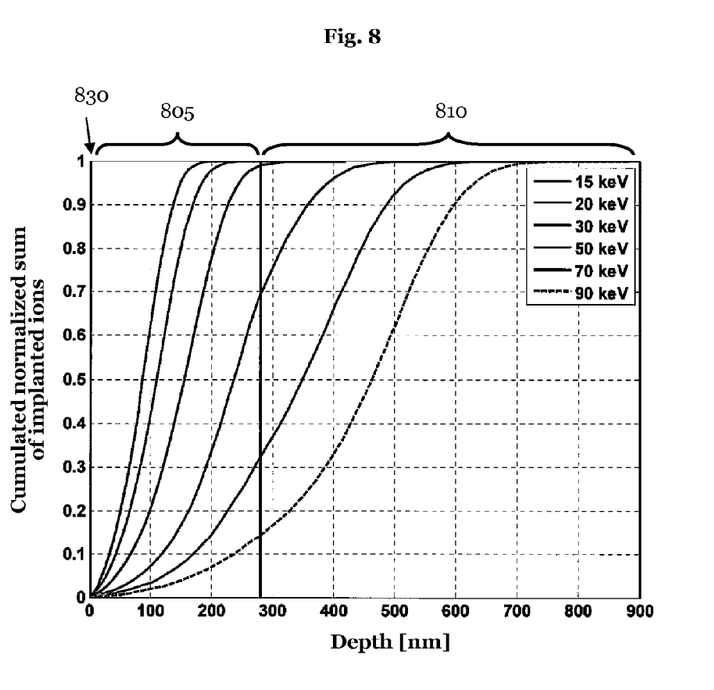
FIG. 8 schematically represents a depth of penetration as a function of the helium beam energy in an EUV mask, wherein helium ions hit on the multilayer of the EUV mask.

FIG. 8 shows a simulation of the depth distribution of a helium ion beam into an EUV mask as a function of the ion energy. The helium beam hits the EUV mask at a position without an absorbing pattern element. The ordinate indicates the cumulated normalized sum of implanted ions. As can be seen from FIG. 2, the EUV mask has a thin capping layer 230 which is denoted with the reference numeral 830 in FIG. 8. The multilayer structure 805 has a width of approximately 280 nm. It is deposited on a substrate 810 having a width in the millimetre range of which only the upper relevant portion is indicated in FIG. 8.

Figure 9:
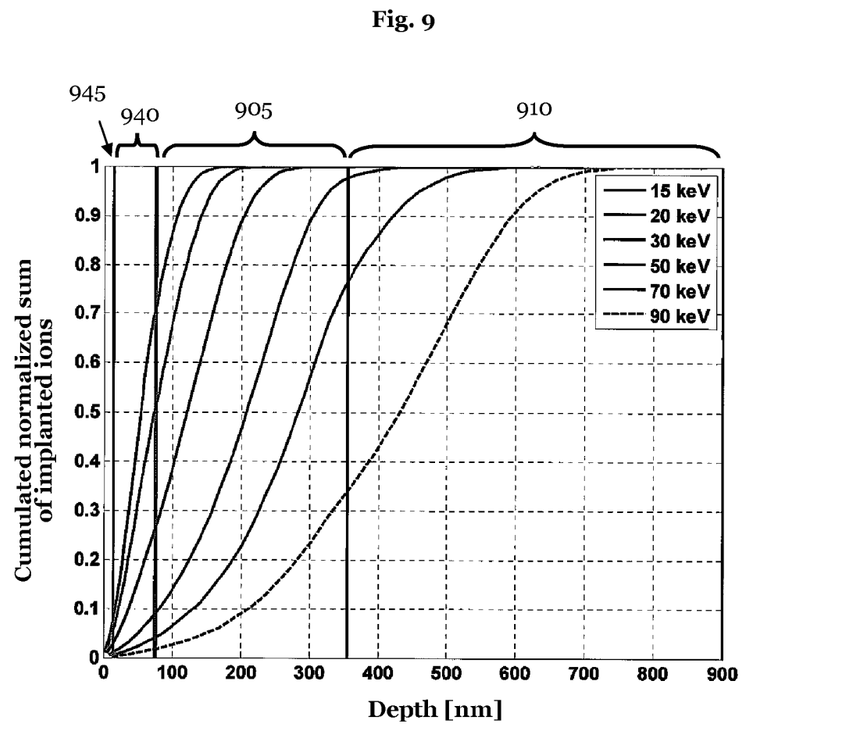
FIG. 9 schematically represents a depth of penetration as a function of the helium beam energy in an EUV mask, wherein helium ions hit on an absorber pattern element of the EUV mask.

FIG. 9 presents a simulation of the depth distribution of a helium ion beam into an EUV mask as a function of the ion energy. The helium beam hits the EUV mask at a position of an absorbing pattern element. Similar to FIG. 8, the ordinate indicates again the cumulated normalized sum of implanted ions. As indicated in FIG. 2, the absorbing pattern 940 has a thin AR layer 945 of a few nanometers arranged on the absorbing pattern elements 940. The absorbing pattern structure 940 has a width of approximately 70 nm. As already mentioned in the context of the discussion of FIG. 2, depending of the absorber material, a thickness of approximately 50 nm is sufficient to basically absorb all incident EUV photons. The multilayer structure 905 and the substrate 910 of FIG. 9 are identical the multilayer 805 and the substrate 810 of FIG. 8.

As can be seen from FIGS. 8 and 9, the depth at which the ions are implanted in the EUV mask depends on the energy with which the ions hit on the surface of the EUV mask. This means that the depth distribution of the implanted ions can be set by selected by the ion beam energy. Further, FIGS. 8 and 9 also reveal that the width of the depth distribution also varies with the energy of the helium beam. Even for ion beam energies of 90 keV the ions are implanted in a way so that more than 50% of the implanted ions are integrated in a depth range of 200 nm. For ion beam energies of 50 keV of less the majority of the build in ions is implanted in a depth range of 100 nm or less.

A comparison of FIG. 8 and FIG. 9 shows that an absorbing pattern element does not significantly change the depth distribution of the implanted helium ions.

The simulations of FIGS. 8 and 9 have been performed with the software program SRIM, which is described in the article "The Stopping and Range of Ions in Solids" by J. F. Ziegler, J. P. Biersack, and U. Littmark, Pergamon Press, New York, 1985.

The implanted dose distribution within an EUV mask can for example be determined by preparing cross-section samples of an EUV mask and investigating the samples with transmission electron microscopy (TEM). The relationship between an exposition of the EUV mask for a predetermined time with predetermined ion beam parameters and the resulting implanted dose distribution within the EUV mask can also be obtained for example from TEM measurements of a series of prepared test samples. This means that the spatial distribution of the implanted ions can be controlled by the selection of the ion beam parameters.

Figure 10:
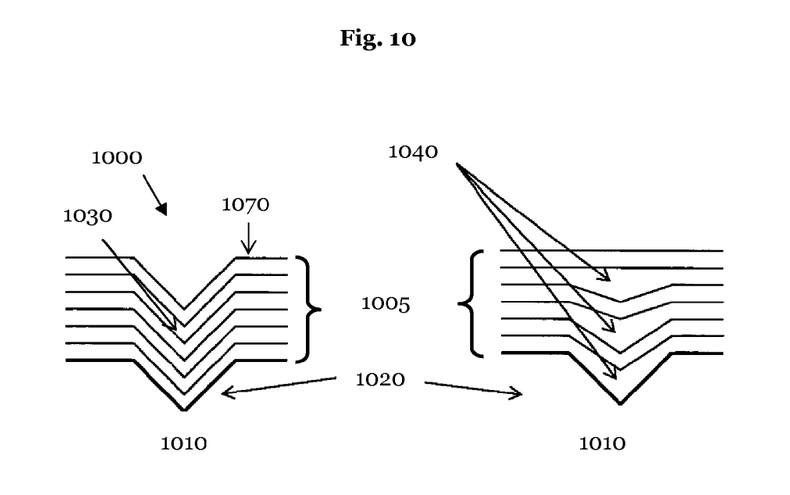
FIG. 10 schematically illustrates the propagation of a buried defect through the multilayer structure of an EUV mask (left) and the action of a volume increase by implanting ions in its multilayer structure.

FIG. 10 schematically shows in the left partial image a pit defect 1020 in a substrate 1020 of an EUV mask 1000. Similar to the FIGS. 3, 4 and 6 the pit defect propagates as defect 1030 through the multilayer structure 1005. The right partial image schematically shows the multilayer structure 1005 after the implantation of ions as for example helium ions. The helium ions are preferably integrated in Si layers 1040 which causes a local increase of the volume of the Si layers 1040. It has been observed that the induced volume change varies as function of the ion species and ion absorbing material. Built-in helium ions in Mo—Si layers predominantly result in a volume expansion of the Si layers 1040. As a result, the local volume expansion of the Si layers 1040 corrects the effect of the pit defect 1020 at the surface 1070 of the multilayer structure 1005.

In the example of FIG. 10, the correction of the pit defect 1020 is performed by a local volume increase of individual Mo layers 1040 of the multilayer structure 1005. This repairing method results in a local breach of the Bragg reflection condition. This problem can be avoided or at least reduced if the ions are preferably implanted in the lowest Mo—Si layers of the multilayer structure 1005 which are close to the substrate 1010. As already explained above, the multilayer structure 1005 shows an asymptotic reflective behaviour. The upper Mo—Si layers close to the surface 1070 of the EUV mask moo contribute the major portion to the reflected EUV radiation, whereas the contribution of the lowest Mo—Si layers is insignificant. Therefore, by correcting the pit defect 1020 of the EUV mask moo by implanting ions in the lowest Mo—Si layers of the multilayer structure 1005 the local breach of the Bragg reflection condition due to the repairing process has a minor effect on the reflectivity of the multilayer structure 1005.

Figure 11:
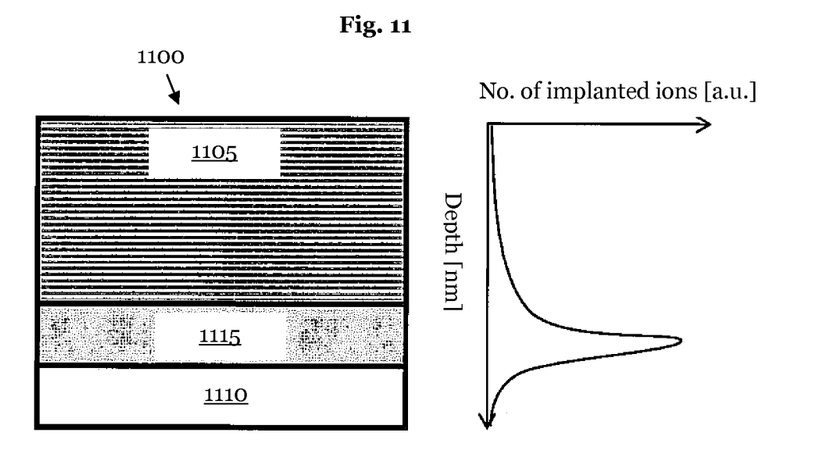
FIG. 11 schematically shows a EUV optical element having a capture layer arranged between the substrate and the multilayer of an EUV mask (left) and schematically illustrates a depth profile of the implanted ions (right)

FIG. 11 schematically illustrates a further approach with allows the repairing of a defect buried in a multilayer without basically distort the reflectivity of the multilayer structure. In the EUV mask 1100 a so-called capture layer 1115 is inserted between the substrate 1210 and the multilayer structure 1105. The capture layer 1115 has a width of approximately several hundred nanometers. Suitable materials for a capture layer are for example silicon (Si) and/or molybdenum disilicide ($MoSi_2$).

It is the purpose of the capture layer 1115 to efficiently capture ions and to provide a large local volume change. The diagram of the right partial image of FIG. 11 schematically presents the depth distribution of the implanted ions. In the thin capture layer 1115 the majority of the ions impinging on the multilayer 1105 is captured and integrated. FIG. 7 depicts that there is a threshold for the ion dose below which a material does not show a volume expansion. Therefore, the depth distribution of the implanted ions (right partial image) indicates that the capture layer 1115 can provide a large local volume expansion which can be adjusted by controlling the beam parameters of the incident ion beam. On the other hand, the doses implanted in the substrate 1110 and in the multilayer structure 1105 are not high enough in order to induce a volume change in these layers.

As already mentioned, the bombardment of a surface with an ion beam leads to a local removal of atoms from the material surface. This effect may be detrimental to a multilayer as the upper Mo—Si layers provide an important contribution to the overall reflectivity of the multilayer structure.

Figure 12:
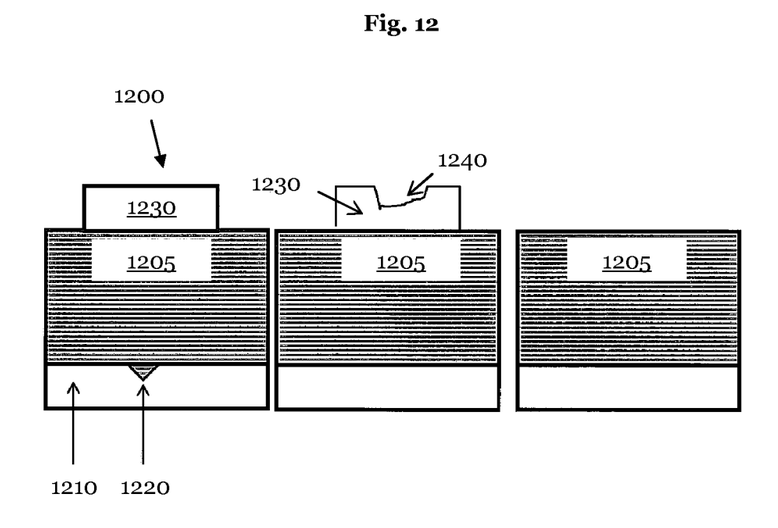
FIG. 12 schematically represents a deposition of protection layer on the multilayer over a pit defect of the substrate (left), schematically shows the protection layer after the repairing of the pit defect (center), and schematically depicts the EUV mask after finalization of the repairing process (right)

FIG. 12 shows an EUV optical element 1200 which can comprise an EUV mask and/or an EUV mirror. The EUV optical element 1200 has as substrate 1210 which has a pit defect 1220 and a multilayer structure 1205. For simplicity reasons the propagation of the buried defect through the multilayer structure 1205 is suppressed. Before starting the defect repairing process by implanting of ions with an incident ion beam, a local protection layer 1230 is deposited on the multilayer structure 1205. As can be seen from a comparison of FIGS. 8 and 9, the use of a thin protection layer does not significantly distort the spatial distribution or depth distribution of the implanted ions.

The protection layer 1230 has a width of at least the lateral dimension of the buried defect and a height of about 100 nm. Preferred materials for a protection layer 1230 are for example carbon (C) and/or tetraethyl orthosilicate (TEOS). The protection layer 1230 is locally deposited on the multilayer structure 1205 by using an electron bean and/or an ion beam in combination with a precursor gas.

After the local deposition of the protection layer 1230, the buried defect 1220 is corrected by implanting an appropriate ion dose in the multilayer structure 1205 as discussed above. The correction of the buried defect 1320 is schematically depicted in the middle part of FIG. 12. The incident ions sputter a portion 1240 of the upper part of the protection layer 1230. Therefore, the protection layer 1230 efficiently protects the surface of the multilayer structure 1205 from the sputter action of the incident ions.

At the end of the ion implantation process, the protection layer 1230 is again removed. This can for example be done by an etching process using an electron beam and/or an ion beam together with one etching gas or a combination of etching gases.

Beside the sputter action at the surface, the interaction of the ions with the material along their path through the material may induce damages in the material along the ion path. Therefore, it can be beneficial to guide the incident ions through portions of a multilayer structure of an EUV optical element whose integrity is of less importance for the reflectivity of the multilayer film.

Figure 13:
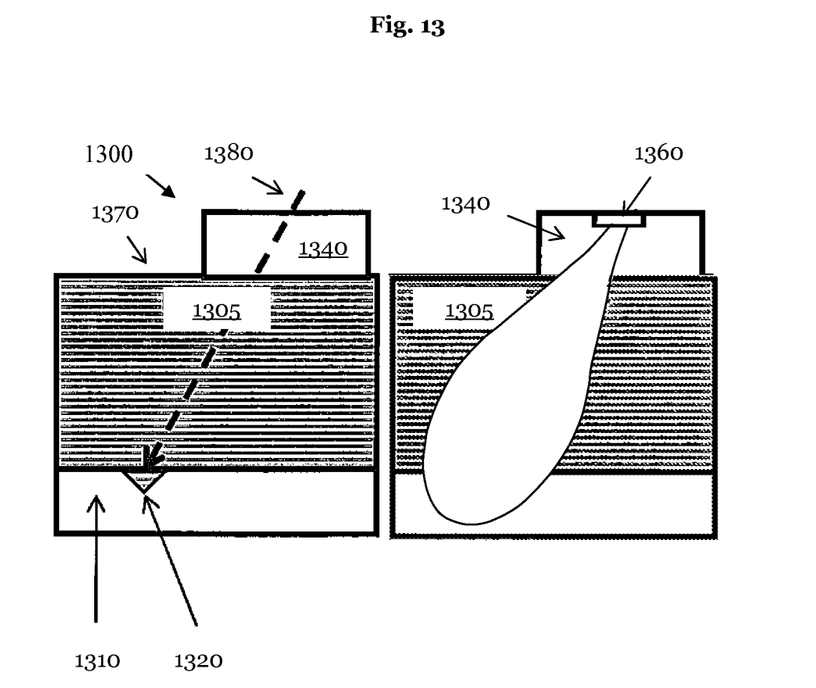
FIG. 13 schematically illustrates the repairing of a pit defect on the substrate of an EUV mask by obliquely directing ions through an absorbing pattern element to a defect (left), and schematically shows the EUV mask at the end of the repairing process having a damaged volume by the interaction of ions with the atoms of the multilayer.

FIG. 13 schematically illustrates an example how such an improvement can be realized for EUV mask 1300. Similar to the left partial image of FIG. 12, the left partial image of FIG. 13 presents again a substrate 1310 having a pit defect 1320. The propagation of the buried defect through the multilayer structure 1305 is again ignored. An absorbing pattern 1340 is deposited on the multilayer film 1305. The buried defect 1320 is not localised below an absorbing pattern element 1340, but below the surface 1370 of the multilayer structure 1305. If an ion beam perpendicularly incidents on the buried defect 1320, it has to pass through the surface 1370 of the multilayer 1305 and may damage the surface 1370 by sputtering atoms from the Mo—Si layers closest to the surface 1370. Furthermore, the ion beam might damage the multilayer structure 1305 along its path to the buried defect 1320 as explained in the preceding paragraph.

FIG. 13 illustrates a configuration with which a possible damage of reflectivity critical portions of the multilayer can at least partially be avoided. The left partial image of FIG. 13 schematically shows the configuration at the beginning of the ion beam irradiation. The ion beam 1380 obliquely impacts on the pattern element 1340 and obliquely crosses the multilayer structure 1305 on its path to the buried defect 1320. The right partial image of FIG. 13 schematically shows the situation at the end of the repairing process. The local volume expansion caused by the implanted ions corrected the buried defect 1320. The surface 1360 of the pattern element 1340 is damaged by the sputter action of the ion beam 1380 during the repairing process. If necessary, the surface damage 1360 of the pattern element 1340 can be corrected by locally depositing absorber material on the damaged surface 1360 by using a method described above.

The white area 1330 below the absorbing pattern element 1340 indicates the area with might be damaged by the interaction of the ions of the ion beam 1380 with the Mo and Si atoms of the multilayer structure 1305. It has a drop shaped form. The major portion of the potentially damaged area is located below the pattern element 1340. In particular, ions do not cross the Mo—Si layers closest to the surface 1370 of the multilayer structure 1305. Thus, by the selected path of the ion beam 1380, the impact of the ion beam 1380 on the reflectivity of the multilayer structure 1305 is minimized.

An EUV mirror which does not have an absorber pattern can also be corrected with the discussed procedure if a protection layer 1230 of FIG. 12 in arranged on the EUV mirror instead of the pattern element 1340.

Finally, the discussed repairing methods can also be applied on defects of a mask blank prior to the deposition of a multilayer structure. By correcting defects existent on the substrate already on the mask blank possible damages of the multilayer structure can be avoided.

The defined method for defect analysis reliably discriminates between surface defects and buried defects of EUV optical elements. Instead of incompletely compensating the impact of buried defects of EUV masks by modifying of the absorbing pattern, the discussed repairing method corrects buried defects by a modification of the substrate and/or of the multilayer structure of EUV optical elements.

The invention claimed is:

1. A method for analyzing a defect of a photolithographic mask for an extreme ultraviolet (EUV) wavelength range (EUV mask), the method comprising:
    a. generating at least one focus stack relating to the defect using an EUV mask inspection tool, wherein the at least one focus stack comprises an image recorded in a focus plane, at least one image recorded above the focal plane, and at least one image recorded below the focal plane;
    b. determining a surface configuration of the EUV mask at a position of the defect;
    c. providing model structures having the determined surface configuration which have different phase errors and generating the respective focus stacks; and
    d. determining a three dimensional error structure of the EUV mask defect by comparing the at least one generated focus stack of the defect and the generated focus stacks of the model structures.

2. The method of claim 1, further comprising applying different repairing methods to the three dimensional error structure and simulating respective focus stacks in order to determine an optimal repairing method.

3. The method of claim 2, further comprising applying the optimal repairing method to the defective position.

4. The method of claim 2, wherein the repairing method comprises at least partially removing the multilayer structure, in particular drilling at least one hole into the multilayer structure.

5. The method of claim 2, wherein the repairing method comprises locally compacting and/or expanding the multilayer structure and/or a substrate of the EUV mask by locally focusing femtosecond laser pulses into the EUV mask.

6. The method of claim 1, wherein the model structures comprise an absorbing pattern structure on a surface of the EUV mask.

7. The method of claim 6, further comprising providing the absorbing pattern structure from EUV mask design data and/or from a recording of at least one image.

8. The method of claim 1, further comprising using a repairing method correcting the three dimensional error structure, so that a resulting multilayer structure is at least approximately corrected to an ideal multilayer structure.

9. The method of claim 8, further comprising applying the repairing method directly onto the defective position of the EUV mask.

10. An inspection microscope for photolithographic masks in the extreme ultraviolet wavelength range adapted to:
    a. generate at least one focus stack relating to the defect using an EUV mask inspection tool, wherein the at least one focus stack comprises an image recorded in a focus plane and at least one image recorded above the focal plane and at least one image recorded below the focal plane;
    b. determine a surface configuration of the EUV mask at a position of the defect;
    c. provide model structures having the determined surface configuration which have different phase errors and generating the respective focus stacks; and d. determining a three dimensional error structure of the EUV mask defect by comparing the at least one generated focus stack of the defect and the generated focus stacks of the model structures.

* * * * *